United States Patent
Kawakami (10) Patent No.: US 9,149,395 B2
(45) Date of Patent: Oct. 6, 2015

(54) LINER FOR INCONTINENCE

(75) Inventor: Yusuke Kawakami, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 250 days.

(21) Appl. No.: 13/819,971

(22) PCT Filed: Aug. 29, 2011

(86) PCT No.: PCT/JP2011/070084
§ 371 (c)(1),
(2), (4) Date: Feb. 28, 2013

(87) PCT Pub. No.: WO2012/029964
PCT Pub. Date: Mar. 8, 2012

(65) Prior Publication Data
US 2013/0165884 A1  Jun. 27, 2013

(30) Foreign Application Priority Data
Aug. 31, 2010 (JP) .................................. 2010-194805

(51) Int. Cl.
*A61F 13/15* (2006.01)
*A61F 13/534* (2006.01)
(Continued)

(52) U.S. Cl.
CPC ............ *A61F 13/534* (2013.01); *A61F 13/4756* (2013.01); *A61F 13/511* (2013.01); *A61F 13/51458* (2013.01); *A61F 13/53* (2013.01); *A61F 2013/530518* (2013.01)

(58) Field of Classification Search
CPC .................... A61F 13/15707; A61F 13/53436; A61F 13/534; A61F 13/536; A61F 13/538
USPC ..................... 604/378, 380, 385.01
See application file for complete search history.

(56) References Cited

U.S. PATENT DOCUMENTS 4,231,357 A * 11/1980 Hessner .......................... 602/47
4,687,478 A *  8/1987 Van Tillburg ................. 604/387
(Continued)

FOREIGN PATENT DOCUMENTS

CN      1823694 A    8/2006
EP      1917939 A1   5/2008
(Continued)

OTHER PUBLICATIONS

International Search Report corresponding to PCT/JP2011/070084, dated Oct. 11, 2011.
Extended European Search Report issued Jun. 3, 2014, corresponds to European patent application No. 11821978.1.

*Primary Examiner* — Jacqueline Stephens
(74) *Attorney, Agent, or Firm* — Lowe Hauptman & Ham, LLP (57) ABSTRACT

A liner for incontinence includes a skin contact side sheet, a non-skin contact side sheet, and an absorbent body arranged between these sheets and including an absorbent material. The absorbent material includes 30 to 70 mass % of SAP. The liner includes a main body and wings in an intermediate region of the main body. An SAP basis weight in the intermediate region is larger than in front and rear regions of the main body. The main body includes a front compressed region which is positioned between the intermediate region and the front region immediately in front of a urinating position (UP) of a wearer when worn, side compressed regions which extend from the intermediate region to the front region and rear region, respectively, and a rear compressed region which extends in the rear region in substantially the width direction. At the compressed regions, the absorbent body is continuous.

7 Claims, 7 Drawing Sheets

(51) Int. Cl.
*A61F 13/514* (2006.01)
*A61F 13/53* (2006.01)
*A61F 13/511* (2006.01)
*A61F 13/475* (2006.01)

(56) References Cited

U.S. PATENT DOCUMENTS

| | | | |
|---|---|---|---|
| 4,950,264 A * | 8/1990 | Osborn, III | 604/385.08 |
| 5,785,696 A | 7/1998 | Inoue et al. | |
| 2003/0236510 A1 | 12/2003 | Yasumura et al. | |
| 2005/0124951 A1 | 6/2005 | Kudo et al. | |
| 2005/0148973 A1 | 7/2005 | Tamura et al. | |
| 2006/0116652 A1 * | 6/2006 | Miura et al. | 604/380 |

FOREIGN PATENT DOCUMENTS

| | | |
|---|---|---|
| JP | 1-195856 A | 8/1989 |
| JP | 8-196559 A | 8/1996 |
| JP | 2002-345888 A | 12/2002 |
| JP | 2002345888 | 12/2002 |
| JP | 2003088550 | 3/2003 |
| JP | 2004-65929 A | 3/2004 |
| JP | 2006-230714 A | 9/2006 |
| JP | 2008-86335 A | 4/2008 |
| JP | 2008-178667 A | 8/2008 |
| JP | 4167406 B2 | 10/2008 |
| JP | 2009-056269 A | 3/2009 |
| JP | 2009-100846 A | 5/2009 |

\* cited by examiner

LINER FOR INCONTINENCE

RELATED APPLICATIONS

The present application is a National Phase of International Application Number PCT/JP2011/070084, filed Aug. 29, 2011, and claims priority from Japanese Application Number 2010-194805, filed Aug. 31, 2010.

TECHNICAL FIELD

The present invention relates to a liner for incontinence.

BACKGROUND ART

Known in the art is a sanitary napkin provided with a liquid permeable skin contact side sheet, a liquid impermeable and moisture permeable non-skin contact side sheet, and an absorbent body which is arranged between these skin contact side sheet and non-skin contact side sheet. The sanitary napkin is provided with a main body which includes the absorbent body, which main body includes a front region, a rear region, and an intermediate region between these front region and rear region, and with a pair of wings for fastening the napkin to clothing, the wings being provided adjoining the intermediate region of the main body and being bent and superposed over the intermediate region when worn (see PLT 1). In this napkin, the napkin is reliably fastened to the clothing by the wings. Further, by using the moisture-permeable non-skin contact side sheet, dampness is suppressed.

CITATION LIST

Patent Literature

PLT 1: Japanese Patent Publication (A) No. 2003-088550

SUMMARY OF INVENTION

Technical Problem

As explained above, when worn, the wings are superposed over the intermediate region of the absorbent body. As a result, at the intermediate region, at the outer side of the absorbent body, the non-skin contact side sheet, clothing, and wings are successively superposed. Therefore, the air permeability at the intermediate region falls and unpreferable dampness is likely to be caused. If large dampness occurs, a rash is likely to be caused at the skin of the wearer. In general, the frequency of changing the liner for incontinence is lower than a sanitary napkin and, therefore, the wearing time of the liner is longer. Therefore, in the case of a liner for incontinence, the above problem is more serious than the case of a sanitary napkin.

Solution to Problem

According to the present invention, there is provided a liner for incontinence provided with a liquid permeable skin contact side sheet, a liquid impermeable and moisture permeable non-skin contact side sheet, and an absorbent body arranged between these skin contact side sheet and non-skin contact side sheet and including an absorbent material, the absorbent material including from 30 to 70 mass % of a super absorbing polymer, wherein the liner includes a main body including the absorbent body, the main body including a front region, a rear region, and an intermediate region between these front region and rear region, and a pair of wings for fastening the liner to clothing, the wings being provided adjoining the intermediate region of the main body and being bent and superposed over the intermediate region when worn, wherein a basis weight of the super absorbing polymer included in an absorbent body part positioned at the intermediate region is larger than a basis weight of the super absorbing polymer included in an absorbent body part positioned at the front region and a basis weight of the super absorbing polymer included in an absorbent body part positioned at the rear region, and wherein the main body includes a front compressed region provided between the intermediate region and front region, positioned immediately in front of a urinating position of the wearer when worn, a pair of side compressed regions provided so as to respectively extend from the intermediate region to the front region and rear region, and a rear compressed region provided at the rear region so as to extend substantially along the width direction.

Advantageous Effects of Invention

It is possible to reliably suppress dampness in the liner for incontinence.

DESCRIPTION OF EMBODIMENTS

Figure 1:
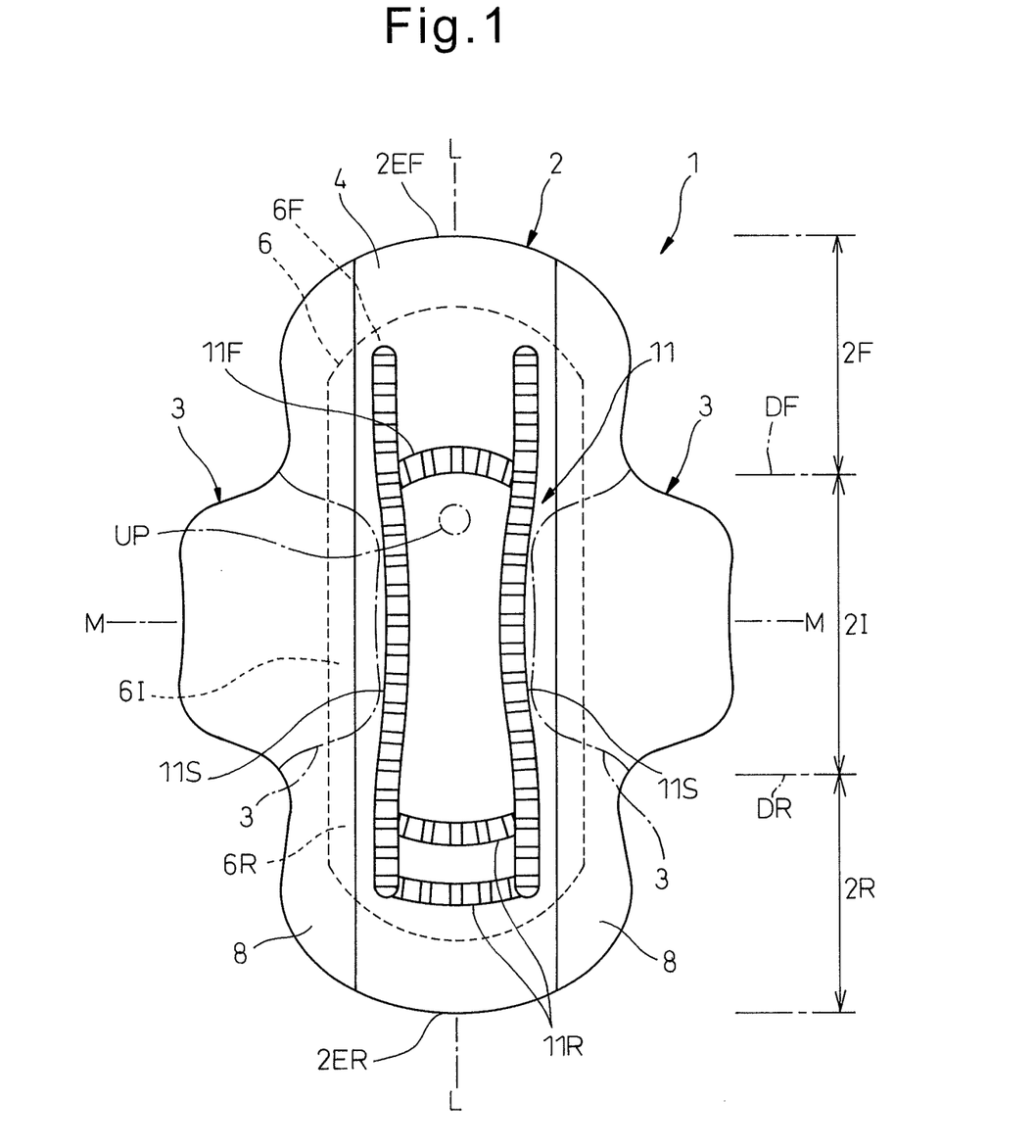
FIG. 1 is a plan view of a liner for incontinence.

Referring to FIG. 1, the liner for incontinence 1 is provided with an oval-shaped main body 2 and a pair of wings 3 which stick out from the side parts of the main body 2 toward the outsides in the width direction.

Figure 2:
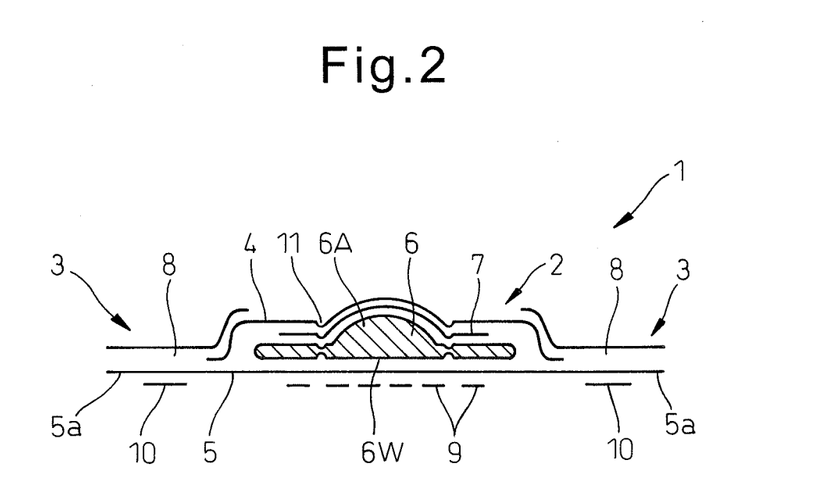
FIG. 2 is a schematic longitudinal cross-sectional view of a liner seen along line M-M of FIG. 1.

In particular, as shown in FIG. 2, the main body 2 is comprised including a skin contact side sheet 4 and a non-skin contact side sheet 5 superposed on each other, an absorbent body 6 arranged between these skin contact side sheet 4 and non-skin contact side sheet 5, and a liquid permeable cushion sheet 7 arranged between the skin contact side sheet 4 and the absorbent body 6. On the other hand, the wings 3 are comprised including parts 5a of the non-skin contact side sheet 5 extending over the side edges of the skin contact side sheet 4 to the outside in the width direction and side sheets 8 superposed on the parts 5a. Here, the skin contact side sheet 4 and non-skin contact side sheet 5 and the non-skin contact side sheet parts 5a and side sheets 8 are respectively joined by for example a hot melt adhesive, heat sealing, etc. Note that, in an embodiment of the present invention, the side sheets 8 are also superposed and joined with the skin contact side sheet 4, therefore the main body 2 also includes the side sheets 8.

Further, the non-skin contact side sheet 5 may also not extend up to the wings 3. In this case, the wings 3 may be comprised of only the side sheets 8 or the side sheets 8 and other sheets superposed with the same.

In an embodiment according to the present invention, the absorbent body 6 is joined with the cushion sheet 7 and non-skin contact side sheet 5 by a hot melt adhesive. In this case, the hot melt adhesive is applied in a mesh shape. As a result, the hot melt adhesive is kept from causing the air permeability to fall.

Figure 3:
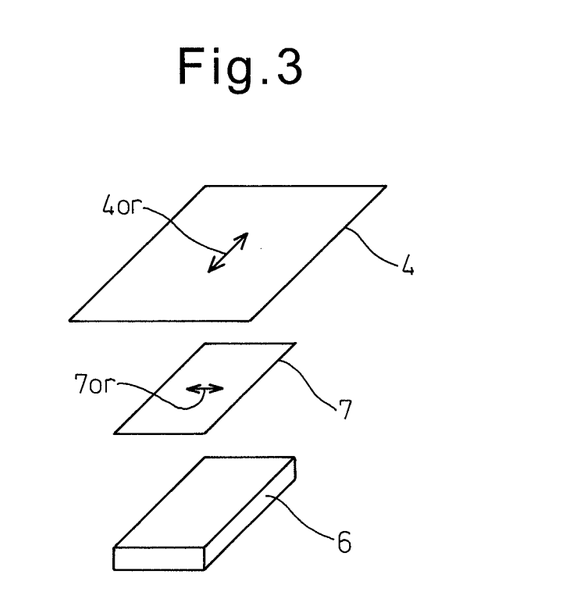
FIG. 3 is a schematic view for explaining fiber orientation.

Further, in an embodiment according to the present invention, the skin contact side sheet 4 and cushion sheet 7 respectively have fiber orientations. The skin contact side sheet 4 and cushion sheet 7 are provided so that these fiber orientations cross to each other. That is, for example, as shown in FIG. 3, the skin contact side sheet 4 and cushion sheet 7 are arranged so that the fiber orientation 4or of the skin contact side sheet 4 extends in substantially the longitudinal direction of the liner 1 and the fiber orientation 7or of the cushion sheet 7 extends in substantially the width direction of the liner 1. In this case, the fiber orientation 4or of the skin contact side sheet 4 and the fiber orientation 7or of the cushion sheet 7 are substantially perpendicular to each other.

Note that the fiber orientation of the sheet can be determined based on the tensile strength of the sheet. That is, samples of the same widths are taken along the longitudinal direction and width direction of the sheet. The tensile strengths of these samples at the time of a certain stretching, for example, 5% or 10% stretching, are measured by a tensile test machine. When the tensile strength of the sample extending along the longitudinal direction of the sheet is higher than the tensile strength of the sample extending along the width direction of the sheet, it can be judged that the fiber orientation of the sheet is along the longitudinal direction, while when the tensile strength of the sample extending along the width direction of the sheet is higher than the tensile strength of the sample extending along the longitudinal direction of the sheet, it can be judged that the fiber orientation of the sheet is along the width direction.

Figure 4:
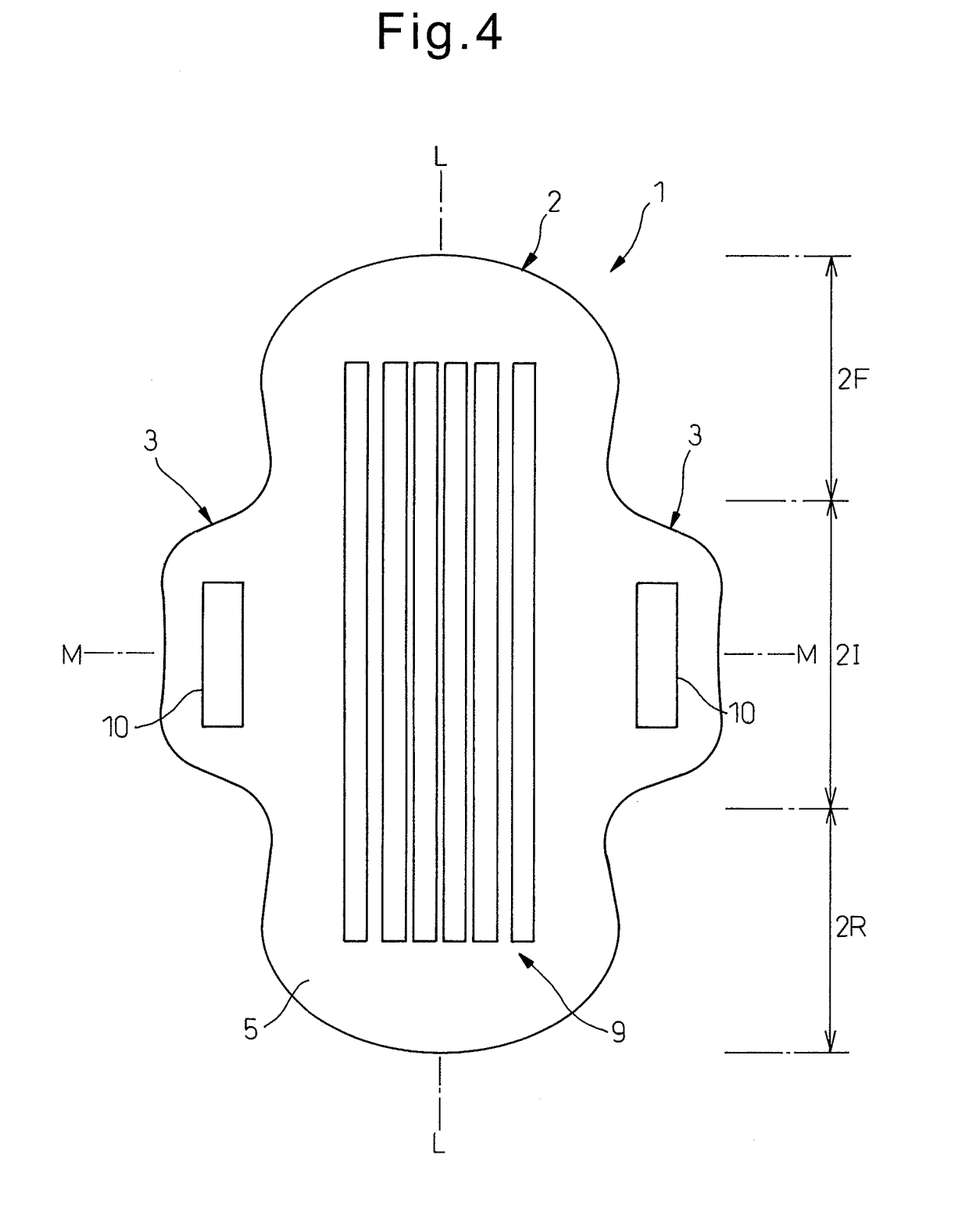
FIG. 4 is a back view of a liner for incontinence.

Further, as shown in FIG. 2 and FIG. 4, at the outer surface of the non-skin contact side sheet 5 corresponding to the back surface of the main body 2, belt-shaped adhesive strips 9 separated from each other in the width direction and extending in parallel in the longitudinal direction are applied, while at the outer surface of the non-skin contact side sheet 5 corresponding to the back surfaces of the wings 3, adhesive strips 10 are applied.

The main body 2, as shown in FIG. 1, includes regions divided from each other by dividing lines DF, DR extending in the width direction, such as a front region 2F, rear region 2R, and intermediate region 2I between these front region 2F and rear region 2R. In this case, the front region 2F is defined between the front end 2EF of the main body 2 and the front dividing line DF, the intermediate region 2I is defined between the front dividing line DF and rear dividing line DR, and the rear region 2R is defined between the rear dividing line DR and the rear end 2ER of the main body 2.

Further, the main body 2 is formed with a compressed region 11 from the skin contact side sheet 4 to the absorbent body 6. The compressed region 11 includes a front compressed region 11F provided extending in substantially the width direction between the intermediate region 2I and the front region 2F, a pair of side compressed regions 11S provided so as to extend from the intermediate region 2I to the front region 2F and the rear region 2R, and for example two rear compressed regions 11R provided to extend in the rear region 2R in substantially the width direction. In an embodiment according to the present invention, the front compressed region 11F and rear compressed regions 11R extend between the side compressed regions 11S.

Figure 5:
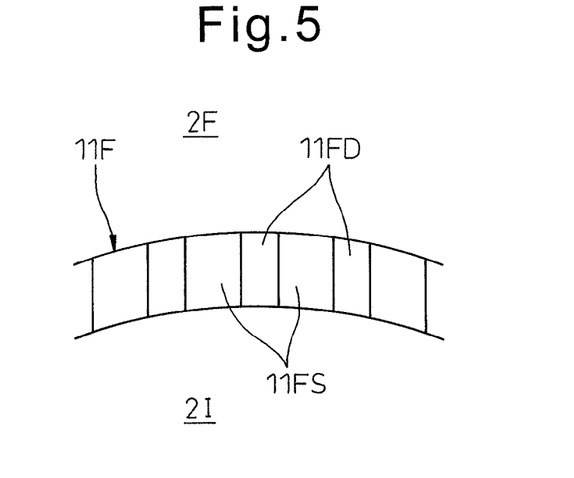
FIG. 5 is a partial schematic enlarged view of a front compressed region.

Further, in an embodiment according to the present invention, the compressed regions 11F, 11S, and 11R are comprised of deep grooves 11FD and shallow grooves 11FS alternately repeating in the length direction. That is, if explaining this taking as an example the front compressed region 11F, as shown in FIG. 5, the front compressed region 11F is comprised of deep grooves 11FD and shallow grooves 11FS which alternately repeat in the length direction. Here, if focusing on the deep grooves 11FD, it is also possible to view this as the front compressed region 11F including a plurality of deep grooves 11FD separated from each other in the width direction. Further, it is also possible to view this as deep grooves 11FD extending between the intermediate region 2I and the front region 2F in substantially the longitudinal direction.

Figure 6:
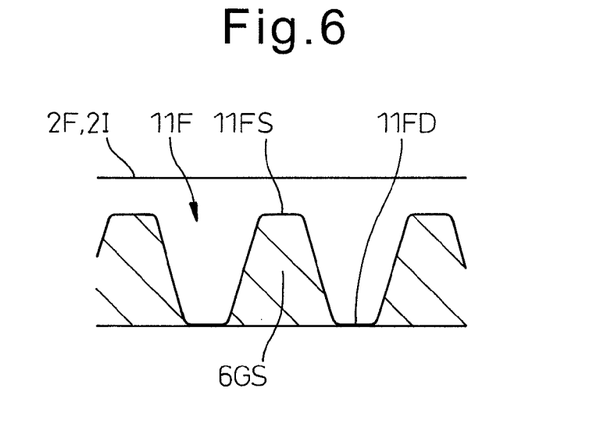
FIG. 6 is a partial schematic cross-sectional view of a front compressed region.
Figure 7:
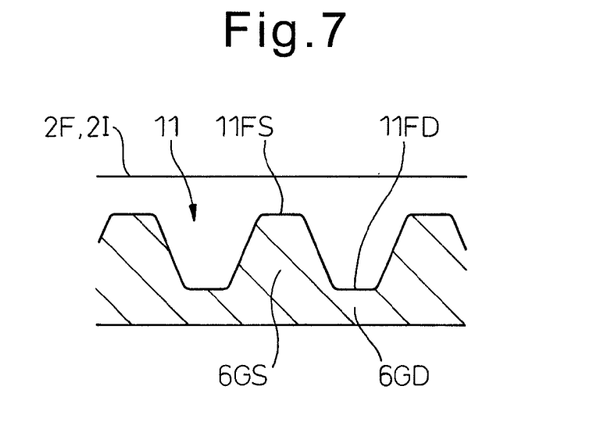
FIG. 7 is a partial schematic cross-sectional view similar to FIG. 6 showing another embodiment.

FIG. 6 and FIG. 7 show embodiments of deep grooves 11FD and shallow grooves 11FS. In the embodiment shown in FIG. 6, there are almost no parts of the absorbent body 6 below the deep grooves 11FD, but parts 6GS of the absorbent body 6 are positioned below the shallow grooves 11FS. On the other hand, in the embodiment shown in FIG. 7, parts 6GS of the absorbent body 6 are positioned below the shallow grooves 11FS, while parts 6GD of the absorbent body 6 are positioned below the deep grooves 11FD. Therefore, in both cases, the absorbent body 6 is continuous at the front compressed region 11F. Note that, if viewing the longitudinal direction of the front compressed region 11F, in the embodiment of FIG. 6, the absorbent body parts 6GS and 6GD are continuous, but in the embodiment of FIG. 7, the absorbent body parts 6GS are discontinuous.

The side compressed regions 11S and rear compressed regions 11R are configured in the same way as the front compressed region 11F. Therefore, at the side compressed regions 11S, the absorbent body 6 is continuous, while at the rear compressed regions 11R as well, the absorbent body 6 is continuous. Note that, the compressed regions 11F, 11S, and 11R may also be configured from deep grooves continuous in the length directions.

Note that, in an embodiment according to the present invention, the liner 1 is formed symmetrically about a longitudinal direction center line L-L and a width direction center line M-M.

The skin contact side sheet 4 has liquid permeability and is, for example, comprised of a woven fabric or nonwoven fabric made of polyethylene (PE), polypropylene (PP), polyethylene terephthalate, or other polyolefin-based thermoplastic hydrophobic fiber, treated to make it hydrophilic, or is comprised of pulp, cotton, or other natural fiber or rayon or another cellulose fiber. In an embodiment according to the present invention, as the skin contact side sheet 4, a 20 to 40 g/m$^2$ air-through nonwoven fabric comprised of PE/PP fiber is used.

The non-skin contact side sheet 5 has liquid impermeability and moisture permeability and is, for example, comprised of a hydrophobic nonwoven fabric, a water impermeable plastic film, a laminate of a nonwoven fabric and water impermeable plastic film, a high waterproof melt blown nonwoven fabric, or a high strength spun bond nonwoven fabric sandwiching an SMS nonwoven fabric. In an embodiment according to the present invention, as the non-skin contact side sheet 5, a 20 to 35 g/m$^2$ or so moisture impermeable PE film is used.

The absorbent body 6 has liquid retention ability and is comprised including an absorbent material 6A and a wrap sheet 6A wrapping the absorbent material 6A (see FIG. 1).

The absorbent material 6A for example is comprised of a fluff pulp or air laid nonwoven fabric and a granular shaped super absorbing polymer (SAP). Here, the fluff pulp is for example comprised of chemical pulp, cellulose fiber, rayon, acetate, or other artificial cellulose fiber, while the air laid nonwoven fabric is for example comprised of pulp and synthetic fiber melt bonded or fixed by a binder to form a nonwoven fabric. The SAP is, for example, comprised of a starch based, acrylic acid based, or amino acid based granular or fibrous polymer. On the other hand, the wrap sheet 6W is a sheet having liquid permeability which is excellent in diffusibility in the liner longitudinal direction, and is, for example, comprised of a sheet having a Klemm water absorbency in the linear longitudinal direction of 10 mm or more. The Klemm water absorbency of the sheet can be measured, for example, according to JIS-P8141. Note that, in an embodiment according to the present invention, the absorbent material 6A and the wrap sheet 6W are bonded with each other by a hot melt adhesive.

Here, if the mass ratio of the SAP to the mass of the absorbent core, that is, the total mass of the pulp and the SAP, is called the "SAP mass ratio", in an embodiment according to the present invention, the SAP mass ratio is set to 30 to 70 mass percent. If the SAP mass ratio is smaller than 30 mass percent, it is difficult to secure an absorbent material density sufficient for imparting liquid diffusibility. If the SAP mass ratio is larger than 70 mass percent, the pulp or other fiber ingredient is relatively insufficient, a gel blocking phenomenon of the super absorbing polymer may easily occur, and therefore the liquid diffusibility is likely to fall or, when worn, the absorbent body is likely to lose its shape due to the external force acting on the absorbent body. Note that, the SAP mass ratio of a sanitary napkin is generally 0 to 10 mass percent, at most 20 mass percent, so the liner for incontinence according to the present invention differs in constitution from a sanitary napkin in this point.

The cushion sheet 7 is for example comprised of a nonwoven fabric made of a polyolefin-based thermoplastic hydrophobic fiber treated to be made hydrophilic. As the nonwoven fabric, an air-through nonwoven fabric, spun bond nonwoven fabric, SMS nonwoven fabric, etc. is used. In an embodiment according to the present invention, as the cushion sheet 7, a 20 to 40 g/m² air-through nonwoven fabric comprised of PE/PP fiber is used.

The side sheets 8 are, for example, comprised of a nonwoven fabric of a polyolefin-based thermoplastic hydrophobic fiber. As the nonwoven fabric, an air-through nonwoven fabric, spun bond nonwoven fabric, SMS nonwoven fabric, etc. are used. In an embodiment according to the present invention, as the side sheets 8, a 15 to 35 g/m² air-through nonwoven fabric comprised of PE/PP fibers is used.

The adhesive strips 9 and 10 are for example comprised of a styrene-isoprene-styrene block copolymer (SIS), styrene-butadiene-styrene block copolymer (SBS), styrene-ethylene-butylene-ethylene copolymer (SEBS), or other hot melt adhesive.

Here, if referring to the parts of the absorbent body 6 positioned at the front region 2F, intermediate region 2I, and rear region 2R respectively as the front part 6F, intermediate part 6I, and rear part 6R (see FIG. 1) and expressing the average SAP basis weight of a part x of the absorbent body 6 by BP(x), in an embodiment according to the present invention, the absorbent body 6 is formed so that $BP(6I) > BP(6F) > BP(6R)$.

Further, if expressing the average absorbent material density of a part x of the absorbent body by D(x), the absorbent body 6 is formed so that $D(6F) > D(6I) > D(6R)$. Note that, the average absorbent material density $D(x)$ (g/m³) of a part x of the absorbent body 6 is obtained by dividing the average basis weight (g/m²) of the absorbent material at the part x by the average thickness (mm) of that part x. In an embodiment according to the present invention, the absorbent material is comprised of pulp and a SAP, so the basis weight of the absorbent material is equal to the total of the basis weights of the pulp and SAP.

Furthermore, if expressing the average thickness of a part x of the absorbent body by T(x), the absorbent material 6 is formed so that $T(6R) < T(6F)$. Note that, the thickness may be measured using a thickness gauge (Ozaki Manufacturing Co., Ltd. Digital Thickness Gauge Model JA-257, measuring ability in specifications claimed to be "1.1N or less"). In this case, it is possible to use a measurement tool of a diameter of 50 mm.

Explaining this more specifically, the absorbent body 6 is, for example, formed by laminating pulp and an SAP in a mold having air porosity, that is, a mesh pattern. This mesh pattern is formed with deep recesses at a position corresponding to the intermediate part 6I of the absorbent body 6, is formed with medium extent recesses at a position corresponding to the front part 6F, and is formed with shallow recesses at a position corresponding to the rear part 6R. As a result, the average SAP basis weight of the intermediate position 6I is larger and the average SAP basis weight of the rear part 6R is smaller. Note that, fine surface relief is sometimes formed on one or both of the front surface and back surface of the absorbent material 6 so the thickness of a part x of the absorbent material 6 is sometimes not uniform. Therefore, in the above explanation, the average thickness is used.

Figure 8:
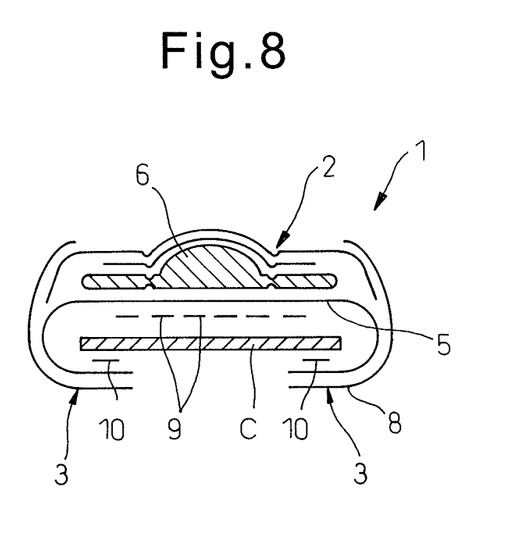
FIG. 8 is a schematic longitudinal cross-sectional view of a liner when worn.

When worn, as shown in FIG. 8, the main body 2 is fastened by the adhesive strips 9 to the inner surface of clothing C such as underwear of the wearer, while the wings 3 are fixed to the outer surface of the clothing C by the adhesive strips 10. That is, the main body 2 and wings 3 sandwich the clothing between them whereby the liner 1 is fastened to the inner side of the clothing C. As a result, wrinkles or twisting can be kept from occurring at the liner 1 when worn, therefore the liner 1 can continue to be reliably fastened to the clothing C over a long period of time. Note that, the clothing to which the liner 1 is fastened generally is panty-shaped with an elastic torso part and leg parts. By fitting over the torso and legs of the wearer, the fabric as a whole fits against the skin of the wearer. As a result, the liner 1 fastened to the inner side of the clothing also is worn in a state fit along the skin of the wearer extending in the front and back direction centered at the hip part.

In this case, the liner 1 is fastened at the crotch part of clothing C at the substantial center in the front-back direction. As a result, the urinating position UP of the wearer (see FIG. 1) is positioned at the intermediate region 2I of the main body 2, in particular a position in the intermediate region 2I near the front region 2F. Therefore, the liquid to be absorbed mainly comprised of urine is mainly absorbed at the intermediate region 6I and diffuses in the intermediate region 6I. In this case, as explained above, the SAP basis weight of the intermediate part 6I is made large, so at the intermediate part 6I, the liquid to be absorbed in reliably absorbed.

At the front of the intermediate part 6I, therefore, right before the urinating position UP, a front compressed region 11F is formed. The absorbent material density at this front compressed region 11F is made higher. As a result, if the liquid to be absorbed which diffuses inside the intermediate part 6I reaches the front compressed region 11F, the liquid to be absorbed is sucked into the front compressed region 11F by capillary action, quickly diffuses inside the front compressed region 11F, and then, flows into the front part 6F.

Here, when the front compressed region 11F is configured as shown in FIG. 6, the liquid to be absorbed 6 moves through the absorbent body part 6GS from the intermediate part 6I to the front part 6F. In this case, the deep grooves 11FD surrounding the absorbent body part 6GS are formed by strongly compressing the absorbent body 6, so even if the absorbent body part 6GS absorbs the liquid to be absorbed and expands, a change in shape of the absorbent body part 6GS is suppressed. On the other hand, when the front compressed region 11F is configured as shown in FIG. 7, the liquid to be absorbed 6 moves through both the absorbent body parts 6GS and 6GD from the intermediate part 6I to the front part 6F. In this case, the absorbent body parts 6GS and 6GD continue in the longitudinal direction of the front compressed region 11F, so diffusion of the liquid to be absorbed is promoted more.

Further, the absorbent material density at the side compressed regions 11S is also higher. As a result, when the liquid to be absorbed diffused inside the intermediate part 6I reaches the side compressed regions 11S, the liquid to be absorbed quickly diffuses through the absorbent body part below the side compressed regions 11S and moves from the width direction center part 6C of the absorbent body 6 (see FIG. 1) to the width direction peripheral parts 6P of the absorbent body 6 (see FIG. 1).

Furthermore, when the side compressed regions 11S are configured like in FIG. 7, the liquid to be absorbed quickly diffuses inside of the absorbent body part below the side compressed regions 11S and moves to the front part 6F and the rear part 6R. In this case, the average absorbent material density D(6F) of the front part 6F is higher than the average absorbent material density D(6R) of the rear part 6R, so the liquid to be absorbed moves easier toward the front part 6F than the rear part 6R.

As a result, the liquid to be absorbed in the intermediate part 6I can be made to move quickly inside the front part 6F and inside the rear part 6R.

Here, referring again to FIG. 1, the above-mentioned wings 3 are positioned adjoining the intermediate region 2I of the main body 2. For this reason, when worn, the bent wings 3 are superposed over the intermediate region 6I of the absorbent body 6 as shown by the dashed-dotted line in FIG. 1. Note that, it is also possible to see this as the intermediate region 2I of the main body 2 being partitioned so as to include parts of the absorbent body 6 where the bent wings 3 are superposed.

As a result, at the intermediate region 6I, as will be understood from FIG. 8, at the outer side of the absorbent body 6, the non-skin contact side sheet 5, the clothing C, and the wings 3 are successively superposed. Therefore, the air permeability at the intermediate region 6I of the absorbent body 6 or the intermediate region 2I of the main body 2 is likely to fall and unpreferable dampness is likely to occur.

However, in an embodiment according to the present invention, as explained above, the liquid to be absorbed which was absorbed at the intermediate part 6I quickly moves to the front part 6F and rear part 6R. As a result, the liquid to be absorbed is widely diffused in the absorbent body 6, that is, it is possible to suppress dampness at the intermediate region 6I. Therefore, the intermediate part 6I or the intermediate region 2I does not have large amounts of moisture and dampness can be reliably suppressed. This means that it is difficult to give an unpleasant feeling to the wearer even when the time the liner 1 is worn is long.

Further, the wrap sheet 6W is comprised of a sheet with excellent diffusibility in the longitudinal direction and is bonded to the absorbent material 6A, so at the wrap sheet 6W as well, the liquid to be absorbed can be broadly diffused.

Further, the fiber orientation 4or of the skin contact side sheet 4 and the fiber orientation 7or of the cushion sheet 7 are substantially perpendicular to each other (see FIG. 3), so due to this as well, broad diffusion of the liquid to be absorbed is secured. That is, at the skin contact side sheet 4, diffusion of the liquid to be absorbed in the longitudinal direction is promoted, while at the cushion sheet 7, diffusion of the liquid to be absorbed in the width direction is promoted.

On the other hand, as will be understood from FIG. 4, the adhesive 9 extends up to the rear region 2R of the main body 2, so the rear region 2R is fastened to the clothing C, but a slight clearance is likely to be formed at the rear region 2R between the liner 1 or skin contact side sheet 4 and the wearer. As a result, moisture can escape through this clearance and dampness can be suppressed.

Further, in an embodiment according to the present invention, the rear region 2R of the main body 2 or the rear part 6R of the absorbent body 6 are formed with rear compressed regions 11R. The rear compressed regions 11R are relatively hard, so inward deformation of the liner 1 is suppressed. As a result, the above-mentioned clearance between the liner 1 and wearer is maintained and dampness can be reliably suppressed.

Figure 9:
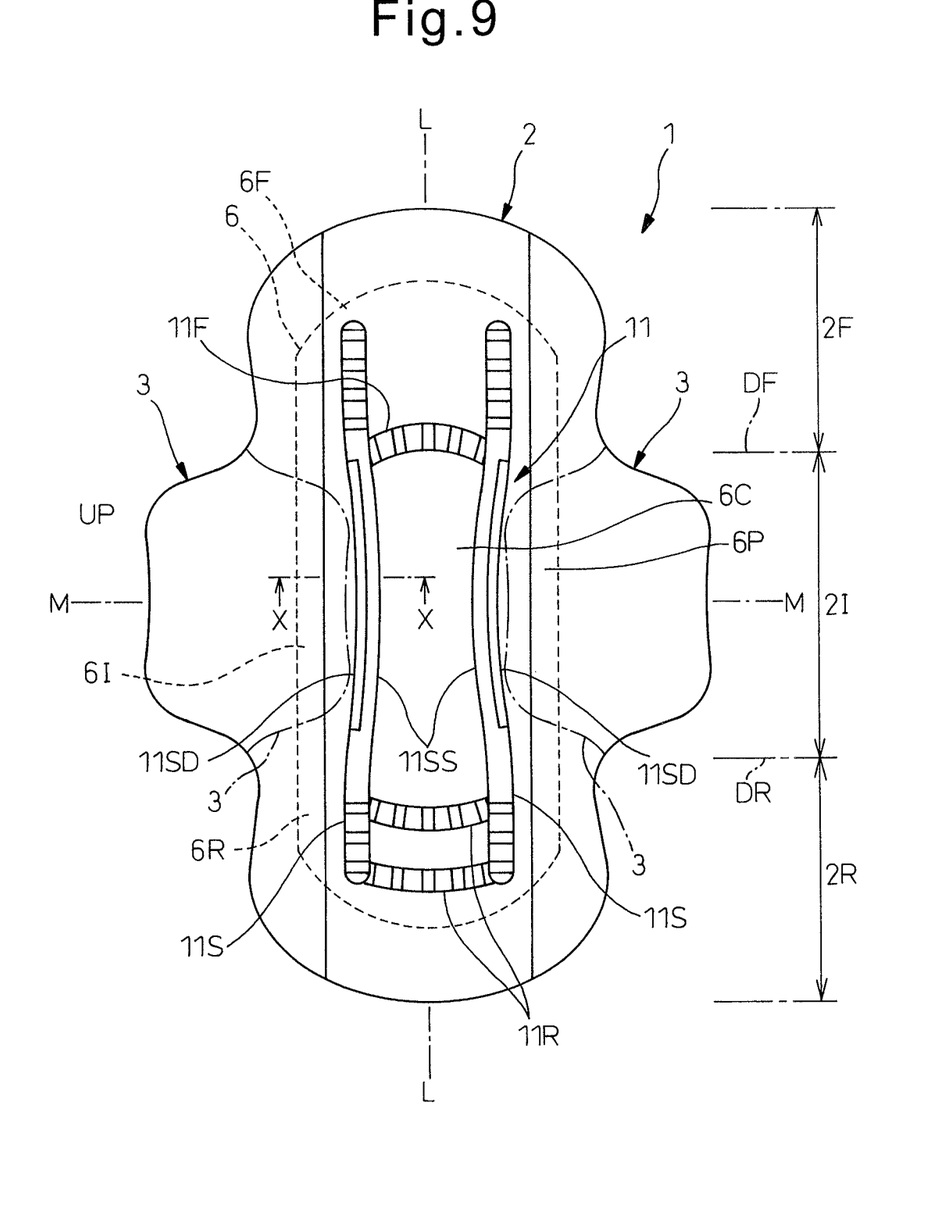
FIG. 9 is a plan view of a liner showing another embodiment of side compressed regions.
Figure 10:
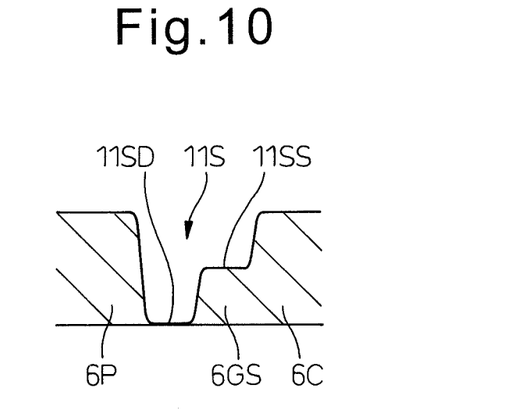
FIG. 10 is a schematic cross-sectional view seen along the line X-X of FIG. 9.

FIG. 9 and FIG. 10 show another embodiment of the side compressed regions 11S. In this embodiment, at the parts of the side compressed regions 11S positioned at the intermediate region 2I or the parts facing the wings 3, strongly compressed regions or deep grooves 11SD and weakly compressed regions or shallow grooves 11SS are formed extending along the longitudinal directions of the side compressed regions 11S. Here, the strongly compressed regions 11SD are formed at the outer sides of the liner 1 in the width direction, while the weakly compressed regions 11SS are formed at the inner side of the liner 1 in the width direction. Further, below the strongly compressed regions 11SD, there are almost no absorbent body parts. Below the weakly compressed regions 11SS, the absorbent body parts 6GS are positioned.

When the liquid to be absorbed at the intermediate part 6I diffuses and next reaches the side compressed regions 11S, the liquid to be absorbed is kept from diffusing outward in the liner width direction by the strongly compressed regions 11SD. As a result, the liquid to be absorbed is kept from diffusing outward in the width direction of the strongly compressed regions 11SD, that is, the regions where the main body 2 and the wings 3 are superposed, therefore it is possible to reliably suppress undesirable dampness.

On the other hand, the liquid to be absorbed reaching the side compressed regions 11S quickly diffuses inside the absorbent body parts 6GS under the weakly compressed regions 11SS in the longitudinal direction and moves to the front part 6F and the rear part 6R. Therefore, the liquid to be absorbed can be made to broadly diffuse and dampness can be reliably suppressed.

The invention claimed is:

1. A liner for incontinence provided with a liquid permeable skin contact side sheet, a liquid impermeable and moisture permeable non-skin contact side sheet, and an absorbent body arranged between these skin contact side sheet and non-skin contact side sheet and including an absorbent material, the absorbent material including from 30 to 70 mass % of a super absorbing polymer, wherein the liner includes a main body including the absorbent body, the main body including a front region, a rear region, and an intermediate region between these front region and rear region, and a pair of wings for fastening the liner to clothing, the wings being provided adjoining the intermediate region of the main body and being bent and superposed over the intermediate region when worn, wherein a basis weight of the super absorbing polymer included in an absorbent body part positioned at the intermediate region is larger than a basis weight of the super absorbing polymer included in an absorbent body part positioned at the front region and a basis weight of the super absorbing polymer included in an absorbent body part positioned at the rear region, wherein the main body includes a front compressed region provided between the intermediate region and front region, positioned immediately in front of a urinating position of the wearer when worn, a pair of side compressed regions provided so as to respectively extend from the intermediate region to the front region and rear region, and a rear compressed region provided at the rear region so as to extend substantially along the width direction, the absorbent body being continuous at these front compressed region, side compressed regions, and rear compressed region, and wherein the liner is further provided with a liquid permeable cushion sheet arranged between the skin contact side sheet and the absorbent body, the skin contact side sheet and cushion sheet have respective fiber orientations, and the fiber orientation of the skin contact side sheet and the fiber orientation of the cushion sheet cross each other.

2. A liner as set forth in claim 1, wherein the front compressed region includes a plurality of compressed parts separated in a width direction.

3. A liner as set forth in claim 1, wherein parts of the side compressed regions positioned at the intermediate region are formed with strongly compressed regions extending along the longitudinal directions of the side compressed regions at the outer sides of the liner in the width direction and with weakly compressed regions extending along the longitudinal directions of the side compressed regions at the inner side in the liner width direction.

4. A liner as set forth in claim 1, wherein the basis weight of the super absorbing polymer included in the absorbent body part positioned at the front region is larger than the basis weight of the super absorbing polymer included in the absorbent body part positioned at the rear region.

5. A liner as set forth in claim 1, wherein an average absorbent material density of the absorbent body positioned at the front region is higher than an average absorbent material density of the absorbent body positioned at the intermediate region.

6. A liner as set forth in claim 1, wherein the absorbent body includes a wrap sheet wrapping the absorbent material, the wrap sheet has liquid permeability and has a Klemm water absorbency in the liner longitudinal direction of 10 mm or more, the absorbent material and the wrap sheet are bonded with each other by a hot melt adhesive.

7. A liner for incontinence provided with a liquid permeable skin contact side sheet, a liquid impermeable and moisture permeable non-skin contact side sheet, and an absorbent body arranged between these skin contact side sheet and non-skin contact side sheet and including an absorbent material, the absorbent material including from 30 to 70 mass % of a super absorbing polymer, wherein the liner includes a main body including the absorbent body, the main body including a front region, a rear region, and an intermediate region between these front region and rear region, and a pair of wings for fastening the liner to clothing, the wings being provided adjoining the intermediate region of the main body and being bent and superposed over the intermediate region when worn, wherein a basis weight of the super absorbing polymer included in an absorbent body part positioned at the intermediate region is larger than a basis weight of the super absorbing polymer included in an absorbent body part positioned at the front region, and the basis weight of the super absorbing polymer included in the absorbent body part positioned at the front region is larger than a basis weight of the super absorbing polymer included in an absorbent body part positioned at the rear region, wherein an average absorbent material density of the absorbent body positioned at the front region is higher than an average absorbent material density of the absorbent body positioned at the intermediate region, wherein the main body includes a front compressed region provided between the intermediate region and front region, positioned immediately in front of a urinating position of the wearer when worn, a pair of side compressed regions provided so as to respectively extend from the intermediate region to the front region and rear region, and a rear compressed region provided at the rear region so as to extend substantially along the width direction, the absorbent body being continuous at these front compressed region, side compressed regions, and rear compressed region, wherein the front compressed region includes a plurality of compressed parts separated in a width direction, wherein parts of the side compressed regions positioned at the intermediate region are formed with strongly compressed regions extending along the longitudinal directions of the side compressed regions at the outer sides of the liner in the width direction and with weakly compressed regions extending along the longitudinal directions of the side compressed regions at the inner side in the liner width direction, wherein the absorbent body includes a wrap sheet wrapping the absorbent material, the wrap sheet has liquid permeability and has a Klemm water absorbency in the liner longitudinal direction of 10 mm or more, the absorbent material and the wrap sheet are bonded with each other by a hot melt adhesive, and wherein the liner is further provided with a liquid permeable cushion sheet arranged between the skin contact side sheet and absorbent body, the skin contact side sheet and cushion sheet have respective fiber orientations, and the skin contact side sheet and cushion sheet are provided so that the fiber orientations cross to each other.

* * * * *